United States Patent [19]

Boyer

[11] 3,996,313

[45] Dec. 7, 1976

[54] HALOGEN CONTAINING PHOSPHORUS MONOOLS

[75] Inventor: Nicodemus E. Boyer, Parkersburg, W. Va.

[73] Assignee: Borg-Warner Corporation, Chicago, Ill.

[22] Filed: Jan. 3, 1975

[21] Appl. No.: 538,337

Related U.S. Application Data

[62] Division of Ser. No. 360,474, May 15, 1973, Pat. No. 3,906,061, which is a division of Ser. No. 55,575, July 16, 1970, Pat. No. 3,758,646.

[52] U.S. Cl. ............................. 260/928; 260/929
[51] Int. Cl.² ..................................... C07F 9/142
[58] Field of Search ........................ 260/928, 929

[56] References Cited

UNITED STATES PATENTS

| | | | |
|---|---|---|---|
| 3,254,142 | 5/1966 | Oertet et al. | 260/928 |
| 3,294,873 | 12/1966 | Lutz et al. | 260/929 |

*Primary Examiner*—Anton H. Sutto
*Attorney, Agent, or Firm*—Cushman, Darby & Cushman

[57] ABSTRACT

Hexa(haloalkyl)mono/hydroxy/alkyl pentaerythritol triphosphite compounds are disclosed. The compounds are prepared by reaction of pentaerythritol alkylene oxide adducts with 3 moles of a tris(haloalkyl)phosphite.

4 Claims, No Drawings

HALOGEN CONTAINING PHOSPHORUS MONOOLS

This is a division of application Ser. No. 360,474 (now U.S. Pat. No. 3,906,061) filed May 15, 1973 which in turn is a division of application Ser. No. 55,575 filed July 16, 1970, now U.S. Pat. No. 3,758,646.

The present invention relates to novel organic phosphites and phosphonates.

The organic phosphites and phosphonates of the present invention are all characterized by having a single hydroxyl group. This hydroxyl group is not on a carbon atom adjacent to a phosphorus atom and is normally linked to the phosphorus atom through a plurality of atoms terminating in an oxygen atom which is directly attached to the phosphorus atom. The phosphites and phosphonates are further characterized by having at least one halogen atom of atomic weight not over 80 attached to a carbon atom attached either directly or indirectly to a phosphorus atom. Preferably the compounds have a plurality of such halogen atoms.

The compounds of the present invention are useful in preparing flame resistant and fire retardant polyesters and polyurethanes. They take part in the reaction forming the polyester or polyurethane and surprisingly even though they are monofunctional, i.e. they have only one hydroxyl group. They do not interfere with the reaction of poly-functional alcohols in reacting with polybasic acids to form polyesters or in reacting with polyisocyanates to form polyurethanes. On the other hand because they take part in the reaction they are permanently bound in the product and cannot be leached out or otherwise removed in the manner that non-reactive halogenated phosphites or phosphonates can be removed.

The novel phosphites and phosphonates also can be used in other formulations, e.g. in amounts 0.1–10% by weight of the polymer as stabilizers against oxidation, light and other polymer degradation for polyvinyl chloride, and other vinyl chloride polymers, e.g. vinyl chloride-vinylidene chloride copolymer (80:20), vinyl chloride-vinyl acetate (87:13), vinyl chloride-acrylonitrile (85:15). In the same proportions they are also stabilizers for monoolefin polymers such as polyethylene, polypropylene, ethylene-propylene copolymers (e.g. 50:50, 80:20 and 20:80), ethylene monoolefin copolymers wherein the monoolefin has 4–10 carbon atoms and is present in a minor amount, e.g. ethylene-butene-1 copolymer (e.g. 95:5) and ethylene-decene-1 copolymer. Furthermore, they can be used in the same amounts to stabilize natural rubber, styrene-butadiene rubber, ethylene-propylene-nonconjugated diene terpolymers, e.g. ethylene-propylene-dicyclopentadiene terpolymer (e.g. 57:42:3), poly cis isoprene, poly cis butadiene, as well as ABS (acrylonitrile-butadiene-styrene) polymer.

The various types of phosphites and phosphonates which are suitable for use in the invention will be discussed in more detail below.

Unless otherwise indicated, all parts and percentages are by weight.

It should be realized that almost all of the compounds of the present invention exist as a mixture of several isomeric forms. Thus the starting dipropylene glycol is commercially available as a mixture of isomers. Similarly many of the halogenated starting materials employed or prepared consist of a plurality of isomers.

In the Arbuzov rearrangement of phosphites to phosphonates there can be used any desired haloalkane such as ethylene dichloride, 2-chloroethanol, chloroform, bromoform, carbon tetrachloride, carbon tetrabromide, octyl fluoride, octyl chloride, octyl bromide, 1,2-dichloropropane, 1,2-dibromopropane, 1,3-dichloropropane, 1,4-dichlorobutane. These halogen compounds can be added in either catalytic amounts, e.g. 0.1 mole per mole of bis(alkyl) diol phosphite (or bis(haloalkyl) diol phosphite) or they can be used in equimolar amounts. In the rearrangement, the haloalkane will react to replace a part of the alkyl or haloalkyl groups, depending on the amount of haloalkane and its boiling point.

It has been found that bis haloalkyl halophosphites such as bis-(2-chloroethyl) phosphorochloridite, bis-(2-bromoethyl) phosphorochloridite, bis(3-chloropropyl) phosphorochloridite, bis(2,3-dichloropropyl) phosphorochloridite react in equimolar proportions with diols, e.g. glycols such as ethylene glycol, propylene glycol, trimethylene glycol, tetramethylene glycol, 1,2-butylene glycol, 1,3-butylene glycol, diethylene glycol, dipropylene glycol, triethylene glycol, tripropylene glycol or the like to form phosphites having a single hydroxyl group such as bis(2-chloroethyl) hydroxyethyl phosphite, bis (2-chloroethyl) hydroxypropyl phosphite, bis(2-chloroethyl) 4'-hydroxybutyl phosphite, bis(2-chloroethyl)2'-hydroxybutyl phosphite, bis(2-chloroethyl) hydroxyethoxyethyl phosphite, bis(2-chloroethyl) hydroxypropoxypropyl phosphite, bis(2-chloroethyl) hydroxy di(ethoxy) ethyl phosphite, bis(2-chloroethyl) hydroxy di(propoxy) propyl phosphite, bis(2-chloroethyl) hydroxy tri(ethoxy) ethyl phosphite, bis(2-chloroethyl) hydroxy tri(propoxy) propyl phosphite, bis(2-bromoethyl) hydroxy di(ethoxy) ethyl phosphite, bis(2,3-dichloropropyl) hydroxyethyl phosphite, bis(2,3-dibromopropyl) hydroxypropoxypropyl phosphite, bis(2-chloroethyl) hydroxyhexyl phosphite. In the reaction hydrogen chloride is eliminated in the form of a salt, e.g. as tertiary amine hydrochloride such as triethylamine hydrochloride. An alternative method for preparing compounds of the above type is to react tris(haloalkyl) phosphites with an equimolar amount of the diol and remove 1 mole of chlorohydrin, e.g. by distillation. The reaction can be carried out in the presence of alkali as a catalyst, e.g. 0.1 mole of sodium methylate. The compounds formed have the formula

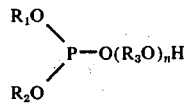

where $R_1$ and $R_2$ are haloalkyl, $R_3$ is alkylene of 2 to 6 carbon atoms and $n$ is an integer such as 1, 2, 3 or 4. $R_1$ and $R_2$ can also be haloaryl such as chlorophenyl, bromophenyl, pentachlorophenyl, dichloronaphthyl or the like. Such compounds are formed for example by reacting

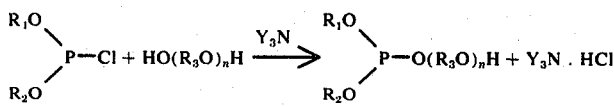

where $Y_3N$ is a tertiary amine. Alternatively the compounds can be formed by the reaction

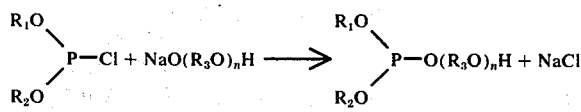

Examples of such compounds are bis(chlorophenyl) hydroxyethyl phosphite, bis(pentachlorophenyl) diethylene glycol phosphite, bis(2,3-dibromophenyl) dipropylene glycol phosphite, bis(2,4-dichloronaphthyl) hydroxypropyl phosphite.

Phosphonates analogous to the above phosphites can be prepared by a conventional Arbuzov rearrangement of the phosphite by heating in the presence of an alkyl halide (it being remembered that the haloaryl groups will not undergo the Arbuzov rearrangement).

Thus there can be formed 2-chloroethyl hydroxyethyl 2-chloroethane phosphonate, 2-chloroethyl hydroxypropyl 2-chloroethane phosphonate, 2-chloroethyl 4'-hydroxybutyl 2-chloroethane phosphonate, 2-chloroethyl 2'-hydroxybutyl 2-chloroethane phosphonate, 2-chloroethyl hydroxyethoxyethyl 2-chloroethane phosphonate, 2-chloroethyl hydroxypropoxypropyl 2-chloroethane phosphonate, 2-chloroethyl hydroxydi-(ethoxy)ethyl 2-chloroethane phosphonate, 2-chloroethyl hydroxydi(propoxy)propyl 2-chloroethane phosphonate, 2-chloroethyl hydroxy tri(ethoxy)ethyl 2-chloroethane phosphonate, 2-chloroethyl hydroxytri(propoxy)propyl 2-chloroethane phosphonate, 2-bromoethyl hydroxydi(ethoxy)ethyl 2-bromoethane phosphonate, 2,3-dichloropropyl hydroxyethyl 2,3-dichloropropane phosphonate, 2,3-dibromopropyl hydroxypropoxypropyl 2,3-dibromopropane phosphonate, 2-chloroethyl hydroxyhexyl 2-chloroethanephosphonate.

By reacting one mole chloroethyl phosphorodichloridite with 2 moles of propylene oxide there is formed 2-chloroethyl bis(2-chloropropyl) phosphite. Transesterification of this with diols, e.g. diethylene glycol, dipropylene glycol, tripropylene glycol, tetramethylene glycol, trimethylene glycol or the other diols set forth above by heating below 100° C. forms ethylene chlorohydrin as the by-product and bis(2-chloropropyl) hydroxyethoxyethyl phosphite, bis(2-chloropropyl) hydroxypropoxypropyl phosphite, bis(2-chloropropyl) hydroxydi(propoxypropyl) phosphite, bis(2-chloropropyl) hydroxybutyl phosphite, bis(2-chloropropyl) hydroxypropyl phosphite. Similar bromine analogues are formed starting from 2-bromoethyl phosphorodibromidite, e.g. bis(2-bromopropyl) hydroxyethoxyethyl phosphite. These compounds upon heating to 100°–150° C. rearrange into the corresponding phosphonates by Arbuzov rearrangement to form 2-chloropropyl hydroxypropoxypropyl 2-chloropropane phosphonate, 2-chloropropyl hydroxyethoxyethyl 2-chloropropane phosphonate, 2-chloropropyl 2'-hydroxybutyl 2-chloropropane phosphonate, 2-bromopropyl hydroxyethoxyethyl 2-bromopropane phosphonate (as well as isomers).

Pentaerythritol alkylene oxide adducts react with 3 moles of a tris(haloalkyl) phosphite to form a hexa(haloalkyl) mono hydroxy alkyl pentaerythritol triphosphite. The equation is as follows using Pluracol PEP 450 (adduct of pentaerythritol with 4 moles of propylene oxide having a molecular weight of about 400):

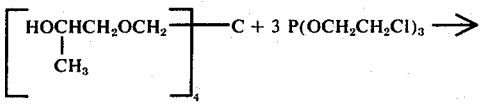

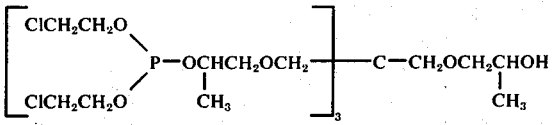

Thus there can be prepared hexa(2-chloroethyl) 2-hydroxypropyl pentaerythritol triphosphite, hexa(2-chloroethyl) hydroxyethyl pentaerythritol triphosphite, hexa(2-chloroethyl) 2-hydroxybutyl pentaerythritol triphosphite, hexa(2,3-dichloropropyl) 2-hydroxypropyl pentaerythritol triphosphite, hexa(2-chloropropyl) 2-hydroxypropyl pentaerythritol triphosphite, hexa(3-chloropropyl) 2-hydroxypropyl pentaerythritol triphosphite, hexa(2-chloroethyl) 3-hydroxypropyl pentaerythritol triphosphite, hexa(2-fluoroethyl)2-hydroxypropyl pentaerythritol triphosphite. The corresponding phosphonates and mixed phosphites-phosphonates are formed by heating the phosphites, e.g. to 140° C. Thus there are prepared penta(2-chloroethyl)2-hydroxypropyl 2-chloroethane pentaerythritol phosphonate diphosphite, tri(2-chloroethyl) 2-hydroxypropyl tri(2-chloroethane) pentaerythritol triphosphonate, penta(2-bromoethyl) 2-hydroxypropyl 2-bromoethane pentaerythritol phosphonate diphosphite. Normally in forming the pentaerythritolalkylene oxide adduct phosphites there will be formed a small amount of the phosphonate-phosphites and/or phosphonates.

EXAMPLE 1

100.0 grams (0.25 mole) of Pluracol PEP 450 and 202.1 grams (0.75 mole) of tris(2-chloroethyl) phosphite were mixed under a nitrogen atmosphere and heated up to 135° C. for 5 hours at 20–50 mm. to distill out 55.0 grams of 2-chloroethanol. The residue was a clear, colorless viscous liquid weighing 230.6 grams and was primarily hexa-(2-chloroethyl) tripropylene hydroxypropyl penaerythritol triphosphite with a small amount of the isomeric phosphonate.

EXAMPLE 1a

The reaction was carried out as in Example 1 except that Pluracol PEP 450 was replaced by 0.25 mole of pentaerythritol. The product was hexa-(2-chloroethyl) pentaerythritol triphosphite, a nearly colorless, viscous liquid.

The polyurethanes prepared using the monool phosphorus compounds of the present invention are useful in making both solid and foamed polyurethanes which are self-extinguishing or non-burning. Thus they can be used to form elastomeric threads, as shock absorbent filling for packages, sound insulation blocks, pipe insulation, upholstery filling material, carpet underlays, hair curlers, blankets, cigarette and pipe filters, pillows, building panels and other forms of insulation, textile linings, toys, cups, protective coatings for wood and steel.

Their greatest utility is in preparing both rigid and flexible polyurethane foams. In preparing polyurethanes there can be used the normal procedure of the preparation of a hydroxyl containing compound with a hydroxyl number between about 20 and 1,000 usually 50 to 700 and thereafter reacting the hydroxyl containing compound with an organic polyisocyanate. The hydroxyl containing material is usually a polyether or a polyester as is well known in the art. The monool phosphite and phosphonates of the invention are usually used in an amount of 2 to 40% by weight of the total hydroxyl compounds but this can be varied. Since only relatively small amounts of the phosphorus monool are needed there is no significant chain termination.

The ratio of NCO/OH usually varies from 0.8–1.2 and is preferably 1.0–1.05:1.

As examples of organic polyisocyanates which can be used to make the polyurethanes there can be employed toluene-2,4-diisocyanate; toluene-2,6-diisocyanate; 4-methoxy-1,3-phenylene diisocyanate; diphenyl methane-4,4'-diisocyanate; 4-chloro-1,3-phenylene diisocyanate; 4-isopropyl-1,3-phenylene diisocyanate; 2,4-diisocyanate-diphenylether; 3,3'-dimethyl-4,4'-diisocyanatodiphenyl methane; mesitylene diisocyanate; durylene diisocyanate; 4,4'-methylene bis(phenylisocyanate); benzidine diisocyanate; 4,4'-diisocyanatodibenzyl; 3,3'-bitolylene-4,4'-diisocyanate; 1,5-naphthylene diisocyanate; cumene-2,4-diisocyanate; 9,10-anthracene diisocyanate; tetramethylene diisocyanate; hexamethylene diisocyanate; decamethylene diisocyanate; toluene-2,4,6-triisocyanate; tritolylmethane triisocyanate; 2,4,4'-triisocyanatodiphenyl ether; phenylene diisocyanate; o-, m-, and p-xylene diisocyanates.

The reaction product of toluene diisocyanate with trimethylolpropane at an NCO/OH ratio of 2:1 (Mondur CB); the reaction product of toluene diisocyanate with 1,2,6-hexanetriol at an NCO/OH ratio of 2:1; the reaction product of toluene diisocyanate with a polyol phosphite at an NCO/OH ratio of 2:1, e.g. when the polyolphosphite is dipropylene glycol tetrol diphosphite or tris-(dipropylene glycol phosphite); as well as polyisocyanates listed in Siefken (Annalen, Vol. 562, pages 122–135, 1949), can be used.

There can also be used polymethylene polyphenylisocyanate, molecular weight 380 to 400, having an isocyanate equivalent of 135 (maximum), a viscosity of 400 centipoises (maximum) at 25° C., a NCO content of 31% (minimum), an acid value (p.p.m. of $H^+$) of 200 (maximum). This material is sold commercially under the trademark PAPI. There can also be used bitolylene diisocyanate (TODI) and dianisidine diisocyanate (DADI).

PAPI is particularly useful in forming rigid polyurethane foams.

Also, there can be used Nacconate 4040, a commercial 2,4-toluenediisocyanate.

Alternatively, as the polyisocyanate there can be used prepolymers made by reacting one or more of the above polyisocyanates with a polyhydroxyl compound. The prepolymers should have terminal isocyanate groups. To insure this, it is frequently desirable to employ an excess of 5% or more of the polyisocyanate in forming the prepolymer.

Typical examples of such prepolymers having isocyanate end groups are those formed from toluene diisocyanate and polyhydroxy compounds. Unless otherwise indicated, in the illustrative examples a mixture of 80% 2,4-isomer and 20% 2,6-isomer of toluene diisocyanate was employed in making the prepolymer. Thus, there can be used the prepolymers from toluene diisocyanate and castor oil, toluene diisocyanate and blown linseed oil, toluene diisocyanate and the polyester of ethylene glycol, propylene glycol and adipic acid having a molecular weight of 1,900 described in Example I of Kohrn U.S. Pat. No. 2,953,839, toluene diisocyanate and polytetramethylene glycol (1,000 molecular weight), toluene diisocyanate and polypropylene glycol (molecular weight 2,025), toluene diisocyanate and dipropylene glycol, toluene diisocyanate and LG-56 (glycerine propylene oxide adduct, molecular weight of 3,000), hexamethylene diisocyanate and pentaerythritol, toluene diisocyanate and sucrose, toluene diisocyanate and polyethylene sebacate, toluene diisocyanate and a mixture of 98% polypropylene glycol molecular weight 1,900 with 2% 1,2,6-hexanetriol, toluene diisocyanate and a copolymer of ethylene oxide and propylene oxide having a molecular weight of 2,000, toluene diisocyanate and a mixture of polypropylene ether glycol molecular weight 995 and castor oil described in Example 2 of Kane U.S. Pat. No. 2,955,091, toluene diisocyanate and tris(dipropylene glycol) phosphite, toluene diisocyanate and tris(octakis(2-hydroxypropyl) sucrose) phosphite, toluene diisocyanate and dipropylene glycol hydroxy propoxypropene phosphonate.

As the polyol material there can be used compounds such as polyethylene glycols having molecular weights of 400 to 3,000, polypropylene glycols having molecular weights of 400 to 3,000, ethylene glycol, diethylene glycol, triethylene glycol, propylene glycol, dipropylene glycol, tripropylene glycol, 1,4-butanediol, thiodiglycol, glycerol, trimethylolethane, trimethylolpropane, ether triols from glycerine and propylene oxide having molecular weights of 1,000 and 3,000 (available commercially as LG-168 and LG-56, respectively), ether containing triols from 1,2,6-hexanetriol and propylene oxide having molecular weights of 750, 1,500, 2,400, and 4,000 (available commercially as LHT 240, LHT 112, LHT 67 and LHT 42, respectively), sorbitolpropylene oxide adduct having a molecular weight of 1,000, pentaerythritol-propylene oxide adduct having a molecular weight of 400 or 1,000, trimethylol phenol, oxypropylated sucrose, triethanolamine, pentaerythritol, diethanolamine, castor oil, blown linseed oil, blown soya oil, N,N,N',N'-tetrakis (2-hydroxyethyl) ethylenediamine, N,N,N',N'-(2-hydroxypropyl) ethylenediamine, mixed ethylene glycol-propylene glycol adipate resin (molecular weight 1,900), polyethylene adipate phthalate, polyneopentylene sebacate, the product made by reacting an excess of 1,4-butanediol with adipic acid and including a small amount of triol, e.g., one molar equivalent of trimethylolpropane for each 3,000 to 12,000 molecular weight units of polyester, polyester from 16 moles adipic acid, 16 moles diethylene glycol and 1 mole of trimethylolpropane, oxypropylated p-tertiary butylphenolformaldehyde resin of Example 2b of de Groote U.S. Pat. No. 2,499,365 and the other oxyalkylated resins of De Groote, tris(dipropylene glycol) phosphite, and tris(polypropylene glycol 2025) phosphite, as well as the polyols disclosed in U.S. Pat. Nos. 3,184,419; 3,194,773; 3,201,358; and 3,385,801.

Foamed polyurethanes can be obtained by adding water prior to or simultaneously with the addition of the organic polyisocyanate.

Alternatively, foams can be prepared by uniformly distributing a liquefied halogen substituted alkane containing at least one fluorine atom in its molecule and which vaporizes at or below the temperature of the foaming mass. Such fluorine containing compounds include trichloromonofluoromethane, dichlorodifluoromethane, dichloromonofluoromethane, chlorodifluoromethane, trichlorotrifluoroethane, dichlorotetrafluoroethane and dichlorohexafluoropropane. The foams can be formed with such fluorine containing compounds in the manner described in General Tire British Pat. No. 821,342 or Barnes U.S. Pat. No. 3,022,256. If desired, water can be used in conjunction with the liquefied fluorine containing haloalkane. Volatile hydrocarbons such as pentane can also be employed as the expanding agent.

The foamed polyurethanes can be made by either the one shot or two step method.

In preparing the cured and/or foamed polyurethanes any of the conventional catalysts can be employed, e.g., sodium hydroxide, sodium methylate, sodium phenolate, tertiary amines, e.g. N-methyl morpholine, N-ethyl morpholine, 1,2,4-trimethylpiperazine, trimethyl amine, triethyl amine, tributyl amine and other trialkyl amines. The esterification product of 1 mole of adipic acid and 2 moles of diethyl ethanolamine, triethyl amine citrate, 3-morpholinopropionamide, 2-diethylamineacetamide, triethylene diamine, N,N,N',N'-tetrakis (2-hydroxypropyl) ethylene diamine, tribenzyl amine, N,N'-dimethylpiperazine, N,N-dimethyl hexahydroaniline, 2,2,1-diazabicyclooctane, 1,2-dimethylimidazole, arsenic trichloride, antimony pentachloride, titanium tetrachloride, dioctyl lead diacetate, octylene glycol titanate can be employed. There can also be used tin compounds having at least one direct carbon to tin valence bond, e.g. hydrocarbon tin acrylates such as dibutyltin dilaurate, dibutyltin dioctoate, tributyltin monolaurate, dimethyltin diacetate, dibutyltin maleate, hydrocarbon tin alkoxides, e.g. dibutyltin diethoxide and dibutyltin dimethoxide, octyl stannoic acid, trimethyltin hydroxide, trimethyltin chloride, triphenyltin hydride, triallyltin chloride, tributyltin fluoride, dibutyltin dibromide, bis(carboethoxymethyl) tin diiodide, tributyltin chloride, trioctyltin acetate, butyltin trichloride, octyltin tris(thiobutoxide), dimethyltin oxide, stannous octanoate, dioctyltin oxide, diphenyltin oxide, stannous oleate, as well as the other tin compounds set forth in Hostettler French Pat. No. 1,212,252 and Barnes U.S. Pat. No. 3,022,256.

There can also be used a small amount, e.g., 0.001 to 10% by weight of the total ingredients of a stabilizing or thickening agent, e.g. methoxylated cellulose, ethyl cellulose, hydroxyethyl cellulose, benzyl cellulose, cellulose acetate, cellulose acetate butyrate, hydroxyethyl polyvinyl alcohol, polyvinyl chloride, polymerized methyl methacrylate.

Fillers can be added in amounts up to 20 percent by weight, e.g., clay, diatomaceous earth, powdered aluminum and beryllium, vermiculite, cork, bark, foamed polystyrene, foamed polyethylene and foamed polypropylene can be used.

Conventional surfactants can be added in an amount of 0.1 to 5% by weight of the composition. Preferably, less than 1%, e.g. 0.2%, of surfactant is employed. The preferred surfactants are silicones, e.g., polydimethyl siloxane having a viscosity of 3 to 100 centistokes, trimethoxydimethyl polysiloxane molecular weight 850 copolymerized with a dimethoxypolyethylene glycol of molecular weight 750 as well as any of the other siloxanes disclosed in Hostettler French Pat. No. 1,212,252 and the siloxane-oxyalkylene copolymers having from about 10 to 80% by weight of siloxane polymer and from 90 to 20% by weight of alkylene oxide polymer such as the copolymers described in U.S. Pat. No. 2,834,748.

What is claimed is:

1. A compound having the formula

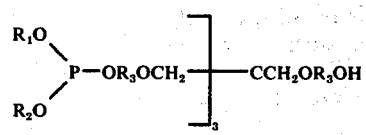

wherein each of $R_1$ and $R_2$ is haloalkyl of 2 to 3 carbon atoms and $R_3$ is lower alkylene of at least 2 carbon atoms, the halogen atoms having an atomic weight up to 80.

2. A compound according to claim 1 wherein $R_1$ and $R_2$ are mono to dihaloalkyl of 2 to 3 carbon atoms and $R_3$ is alkylene of 2 to 3 carbon atoms.

3. A compound according to claim 2 wherein $R_1$ and $R_2$ are 2-chloroethyl and $R_3$ is propylene.

4. A member of the group consisting of (1) the reaction product of one mole of a pentaerythritol alkylene oxide adduct with 3 moles of a tris (halo 2 to 3 carbon atom alkyl) phosphite, the halogen having an atomic weight of up to 80 and (2) a phosphonate isomeric with (1).

* * * * *